(12) United States Patent
Meads

(10) Patent No.: US 11,207,224 B1
(45) Date of Patent: Dec. 28, 2021

(54) PORTABLE SANITARY STAGING ASSEMBLY

(71) Applicant: Saneepad LLC, Dallas, TX (US)

(72) Inventor: Russell Meads, Aventura, FL (US)

( * ) Notice: Subject to any disclaimer, the term of this patent is extended or adjusted under 35 U.S.C. 154(b) by 403 days.

(21) Appl. No.: 15/851,035

(22) Filed: Dec. 21, 2017

Related U.S. Application Data

(60) Provisional application No. 62/437,789, filed on Dec. 22, 2016.

(51) Int. Cl.
| | | |
|---|---|---|
| *A61F 13/15* | (2006.01) | |
| *A61F 13/551* | (2006.01) | |
| *A61F 13/00* | (2006.01) | |
| A61F 17/00 | (2006.01) | |
| A61F 15/00 | (2006.01) | |
| A47K 10/32 | (2006.01) | |
| A47D 5/00 | (2006.01) | |
| A61F 13/84 | (2006.01) | |

(52) U.S. Cl.
CPC ...... *A61F 13/551* (2013.01); *A61F 13/00042* (2013.01); *A47D 5/00* (2013.01); *A47K 10/32* (2013.01); *A61F 13/5519* (2013.01); *A61F 13/84* (2013.01); *A61F 15/001* (2013.01); *A61F 17/00* (2013.01); *A61F 2013/16* (2013.01); *A61F 2013/55155* (2013.01); *A61F 2013/8402* (2013.01)

(58) Field of Classification Search
CPC .... A61F 13/551; A61F 13/5515; A61F 13/84; A61F 13/5519; A61F 13/0042; A61F 2013/5515; A61F 2013/8402; A61F 15/001; A61F 17/00; A61F 2013/16; A47D 5/00; A47K 10/32

USPC .......... 604/385.06, 385.02, 385.13
See application file for complete search history.

(56) References Cited

U.S. PATENT DOCUMENTS

| | | | | |
|---|---|---|---|---|
| 2005/0138894 A1* | 6/2005 | Snell | ........... | A61F 13/8405 53/412 |
| 2013/0312197 A1* | 11/2013 | Sanders | ........... | A47G 9/1045 5/655 |
| 2014/0228797 A1* | 8/2014 | Beresford | ........... | A61F 13/84 604/385.06 |

FOREIGN PATENT DOCUMENTS

| | | | | |
|---|---|---|---|---|
| CA | 2853533 | * | 5/2014 | ........... A61F 13/84 |

* cited by examiner

*Primary Examiner* — Jacqueline F Stephens
(74) *Attorney, Agent, or Firm* — Malloy & Malloy, P.L.; Peter A. Matos

(57) ABSTRACT

A portable sanitary staging assembly is utilized to place an infant or a baby on while changing a diaper, or to stage an injured person or animal, such as for triage or emergency medical treatment in the field, or for a person or animal receiving medical attention outside of a typical medical environment. A portable sanitary staging assembly includes a sanitary paper dispenser assembly having a dispenser/protector tube dimensioned to receive sanitary paper therein, the dispenser/protector tube having a dispenser slot formed through a portion of the dispenser/protector tube to facilitate dispensing the sanitary paper. A sanitary pad assembly having a main sanitary pad is interconnected to a portion of the sanitary paper dispenser assembly. A cutter mechanism is affixed to a portion of the portable sanitary staging assembly to facilitate removal and disposal of soiled sanitary paper after use.

20 Claims, 8 Drawing Sheets

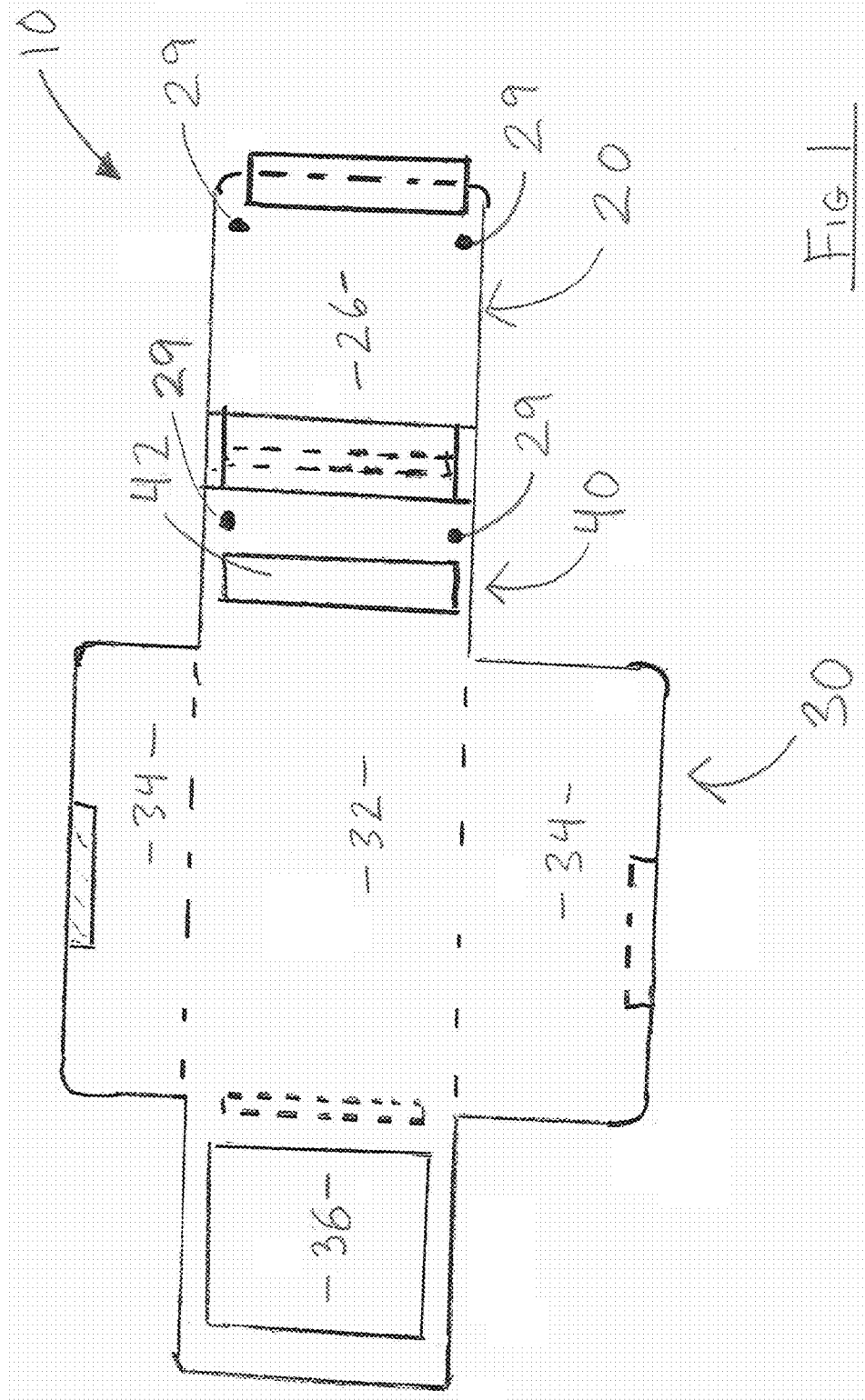

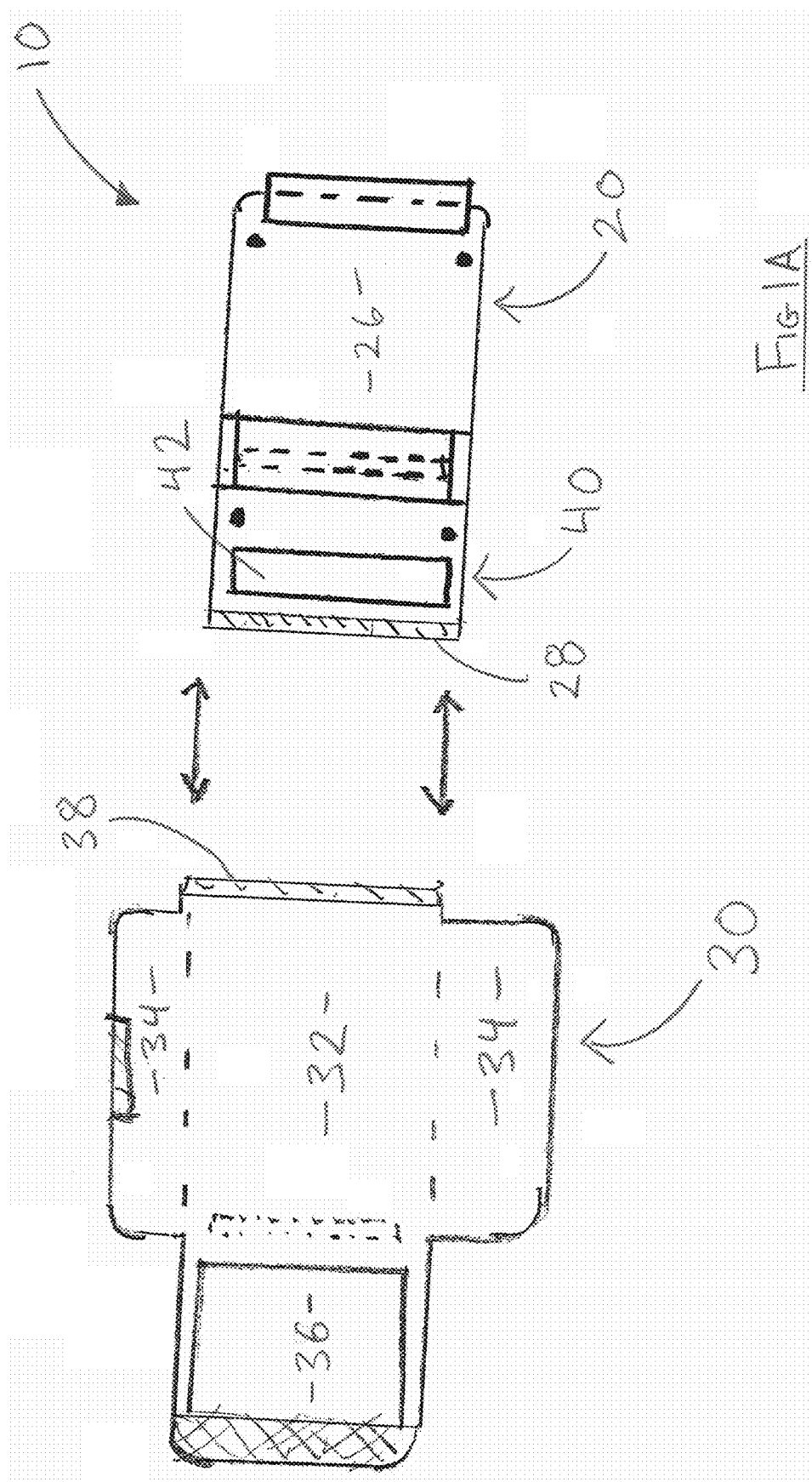

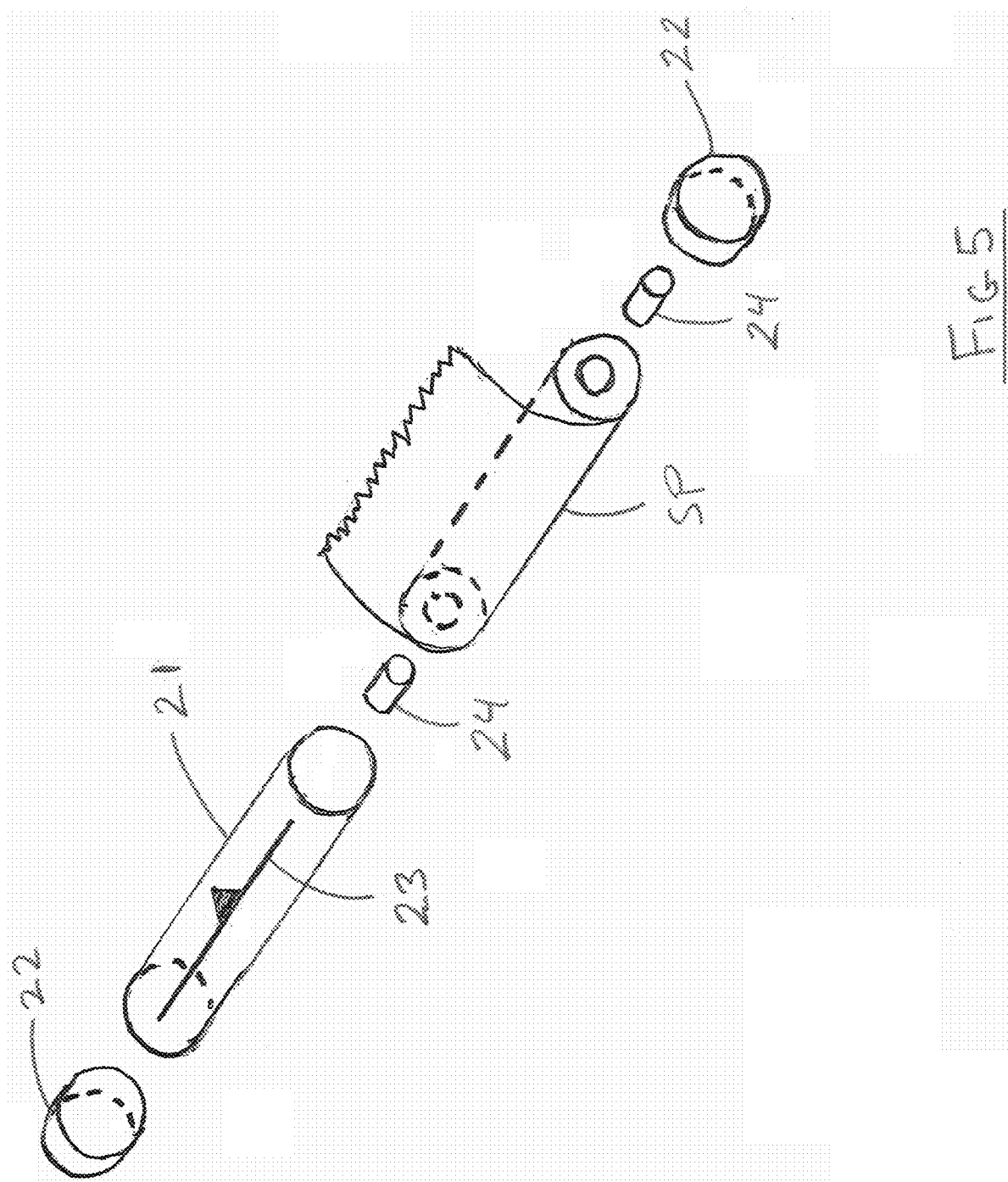

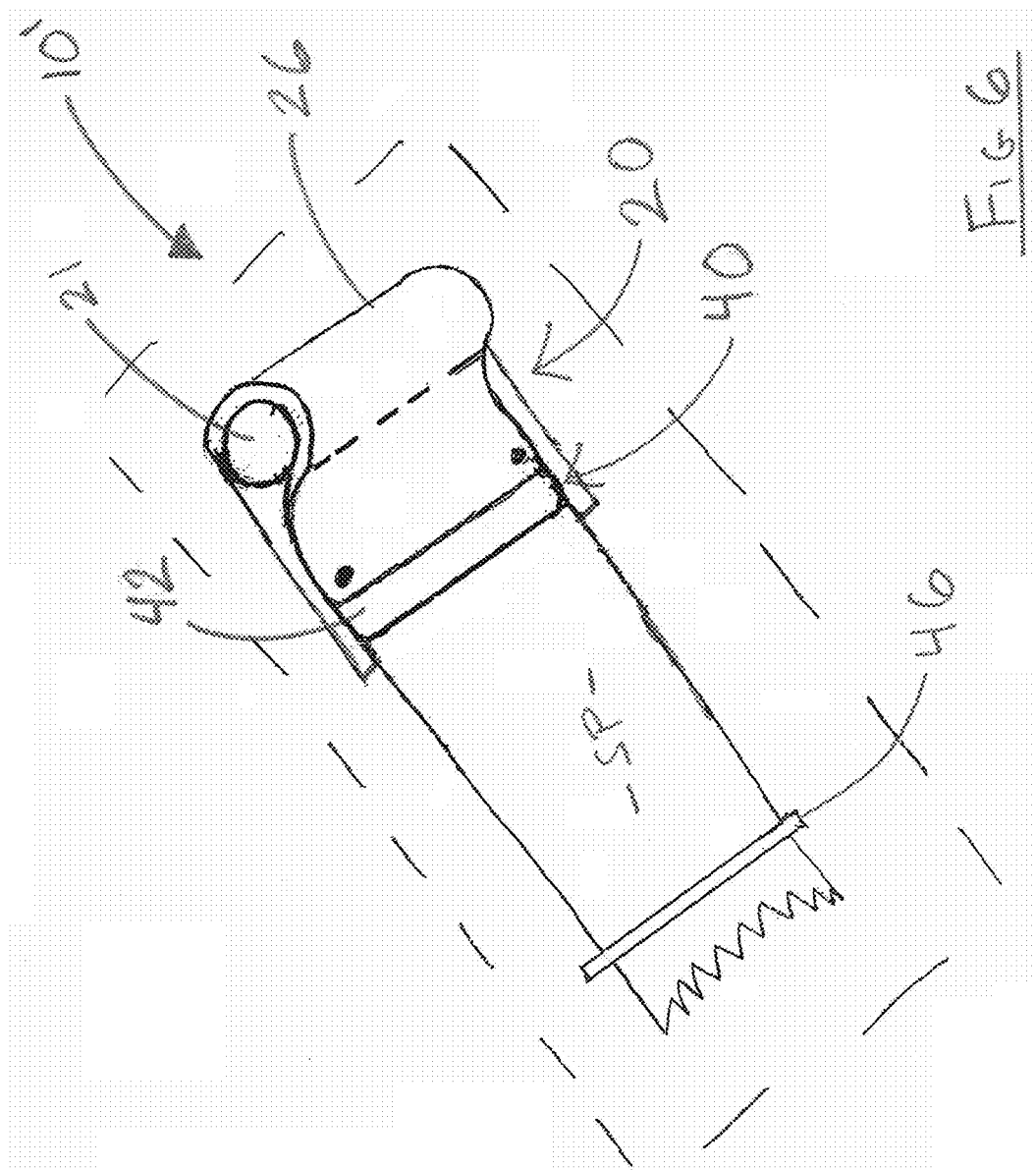

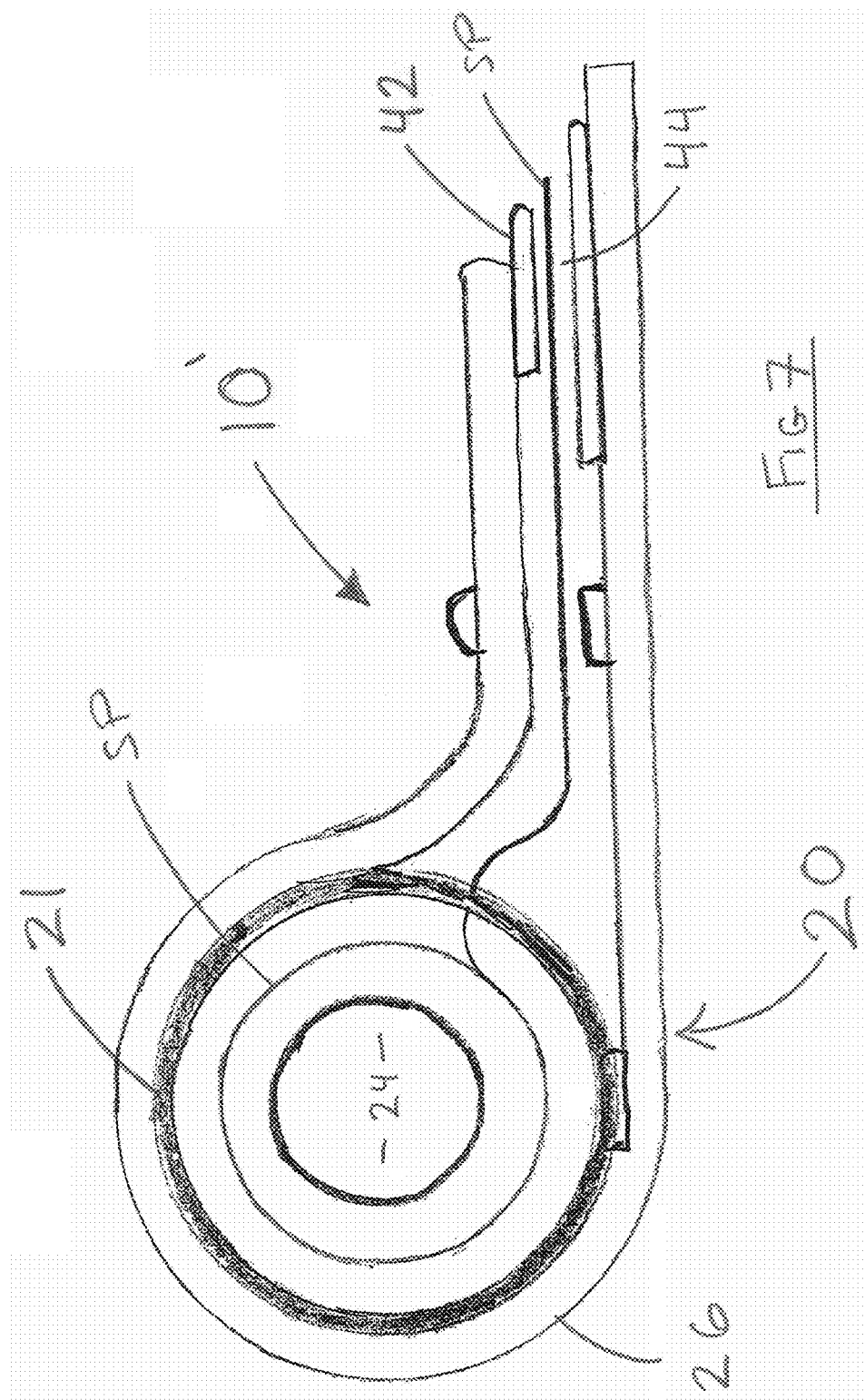

PORTABLE SANITARY STAGING ASSEMBLY

BACKGROUND OF THE INVENTION

Field of the Invention

A portable sanitary staging assembly includes a sanitary paper dispenser assembly to store an amount of sanitary paper therein, and to facilitate dispensing an amount of sanitary paper as needed therefrom. A sanitary pad assembly may be interconnected to the sanitary paper dispenser assembly to provide a sanitary staging area on which a baby may be placed while changing, or on which a person or animal may be staged while receiving medical attention. A cutter mechanism is provided to facilitate removal of soiled sanitary paper after use.

DESCRIPTION OF THE RELATED ART

A common problem faced by parents or other persons responsible for the care of infants and young babies is where to place the infant or baby while his or her diaper is being changed while away from the home. Although permanent changing stations are commonly positioned in an infant's or baby's room at its primary residence, such changing stations are rarely readily available while the parent or person responsible for the infant or baby is traveling with the infant or baby.

When traveling with an infant or baby, it is also common to carry a large bulky diaper bag including a number of clean diapers, baby powder, baby oil, sanitary wipes, and other such ancillary items common for the infant's or baby's care. Baby changing pads are available and often add to the bulk of the contents of the diaper bag. Such baby changing pads typically have an outer washable cover over a foam type insert which may be cleaned and sanitized after use. Unfortunately, however, the parent or responsible person is typically forced to carry a soiled changing pad around in the large bulky diaper bag until they return to their home or other place of residence.

As such, it would be highly beneficial to provide a portable sanitary staging assembly which parents or other responsible persons can utilize when changing an infant's or baby's diaper outside of the home or other residence. It will be further helpful to provide a portable sanitary staging assembly including a supply of sanitary paper on which an infant or baby may be positioned while his or her diaper is being changed, and which may subsequently be removed and readily be disposed of with the soiled diaper. A further advantage may be realized by providing a portable sanitary staging assembly which may also be used to store a plurality of ancillary items necessary while changing an infant's or baby's diaper including, but not limited to, clean diapers, baby powder, baby oil, sanitary wipes, etc.

It would also be beneficial to provide a portable sanitary staging assembly including a supply of sanitary paper on which an injured person or animal, such as for triage or emergency medical treatment in the field, or to stage a person or animal receiving medical attention outside of a typical medical environment, wherein the soiled sanitary paper may be easily removed and disposed of and a fresh clean supply of sanitary paper may be dispended and readied for the next person or animal requiring medical attention.

SUMMARY OF THE INVENTION

The present invention, in one embodiment, is directed to a portable sanitary staging assembly which is easily transported and/or stored and utilized to stage an infant or baby thereon while changing his or her diaper. In one further embodiment, a portable sanitary staging assembly is utilized to stage an injured person or animal, such as for triage or emergency medical treatment in the field, or to stage a person or animal receiving medical attention outside of a typical medical environment. A portable sanitary staging assembly includes a sanitary paper dispenser assembly having a dispenser/protector tube dimensioned to receive an amount of sanitary paper therein. A dispenser/protector tube in accordance with one embodiment of the present invention comprises a dispenser slot formed through a portion thereof to facilitate dispensing of fresh sanitary paper as needed. In accordance with at least one embodiment of the present invention, a sanitary pad assembly includes a main sanitary pad which is interconnected to a portion of the sanitary paper dispenser assembly. In one further embodiment, one or more sanitary flaps are attached to the sanitary main pad to provide additional sanitary staging area when the sanitary flap or flaps is/are disposed in an open orientation. A cutter mechanism is affixed to a portion of the portable sanitary staging assembly to facilitate removal of soiled sanitary paper after use.

One alternate embodiment of a portable sanitary staging assembly in accordance with the present invention is as described above, however, a sanitary pad assembly is not included so as to further facilitate ease of transport and/or storage thereof.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a top plan view illustrative of one embodiment of a portable sanitary staging assembly disposed in a fully expanded orientation in accordance with the present invention.

FIG. 1A is a top plan view illustrative of another embodiment of a portable sanitary staging assembly disposed in a fully expanded orientation wherein a sanitary paper dispenser assembly and a sanitary pad assembly are detachable from one another in accordance with the present invention.

FIG. 5 is an exploded perspective view of the embodiment of the dispenser/protector tube of FIG. 4.

FIG. 6 is a perspective view illustrative of one alternate embodiment of a portable sanitary staging assembly in accordance with the present invention.

FIG. 7 is a side elevation of the alternate embodiment of the portable sanitary staging assembly of FIG. 6 in accordance with the present invention.

DETAILED DESCRIPTION OF THE PREFERRED EMBODIMENT

Figure 2:
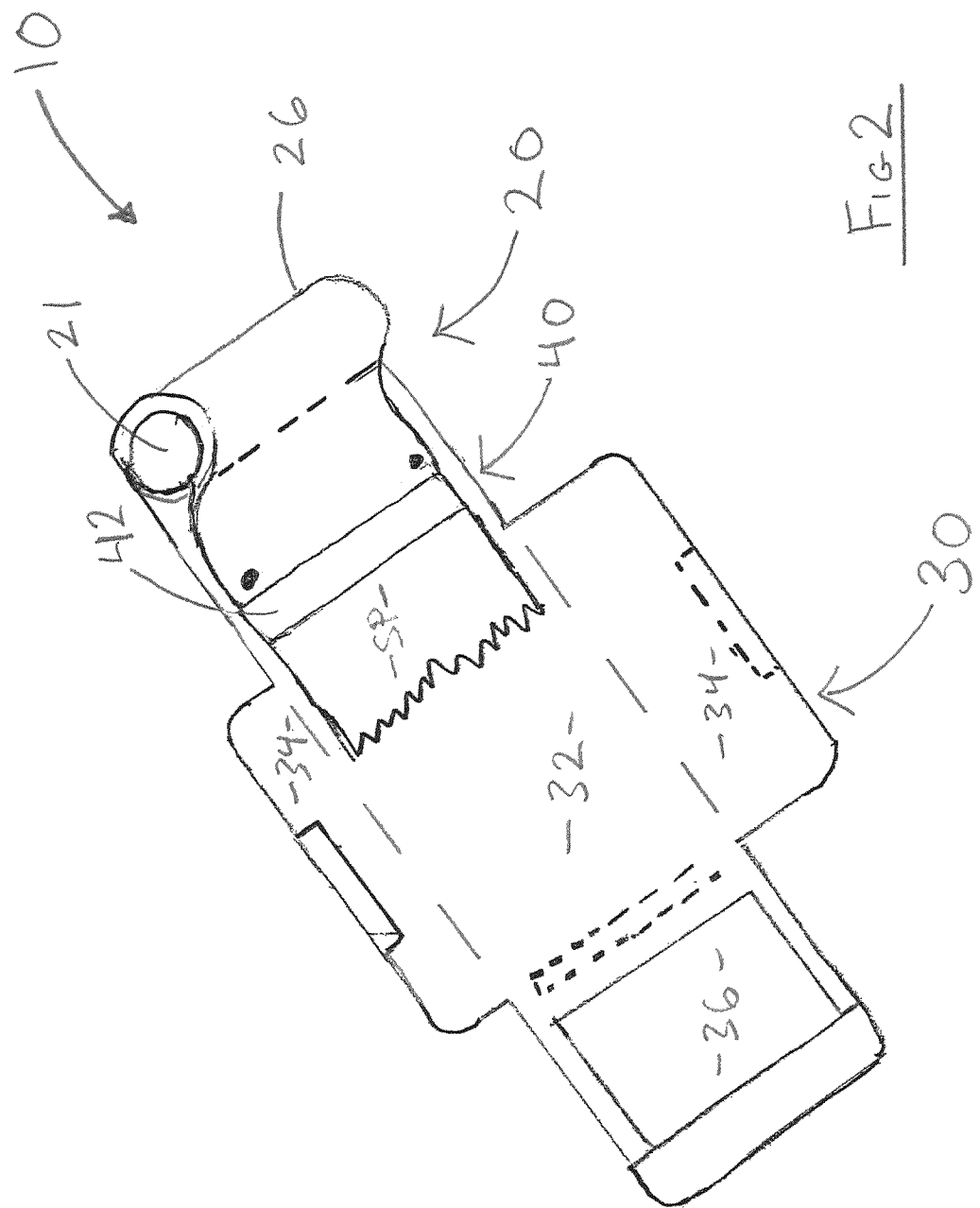
FIG. 2 is a perspective view illustrative of the portable sanitary staging assembly of FIG. 1 disposed in an open orientation in preparation for staging a person thereon in accordance with the present invention.

As previously stated, the present invention is directed to a portable sanitary staging assembly, such as is generally shown as at 10 throughout the figures. A portable sanitary staging assembly 10 in accordance with one embodiment of the present invention may be utilized as a baby changing station. In one other embodiment, a portable sanitary staging assembly 10 in accordance with the present invention is utilized to stage an injured person or animal, such as for triage or emergency field medical treatment, or for staging a person or animal receiving medical attention outside of a typical medical environment.

With reference to the illustrative embodiment of FIG. 1, a portable sanitary staging assembly 10 in accordance with the present invention includes a sanitary paper dispenser assembly 20. With further reference to FIG. 1, a portable sanitary staging assembly 10 in accordance with at least one embodiment of the present invention further comprises a sanitary pad assembly 30. As may also be seen from FIG. 1, a portable sanitary staging assembly 10 in accordance with one embodiment of the present invention further comprises a cutter mechanism 40.

FIG. 1 is illustrative of the sanitary paper dispenser assembly 20 having a dispenser cover 26 disposed in an open and expanded orientation. Looking further to the illustrative embodiments of FIG. 2, the dispenser cover 26 is disposed in a closed operative orientation. As further shown in the illustrative embodiment of FIG. 2, the sanitary paper dispenser assembly 20 comprises a dispenser/protector tube 21 disposed in an operative orientation within the dispenser cover 26. As may be seen from the illustrative embodiment of FIG. 1, dispenser cover 26 comprises a plurality of cooperatively disposed snaps 29 to facilitate disposition of the dispenser cover 26 into a closed operative positon, such as is illustrated best in FIGS. 2 and 6. It will be appreciated by those of skill in the art that other types of mechanical fastener may be employed to facilitate disposition of the dispenser cover 26 into a closed operative position including, by way of example only, ties, zippers, hook and loop type fasteners, magnets, etc. In one further embodiment, a dispenser cover 26 may be permanently formed into a closed operative position.

Figure 3:
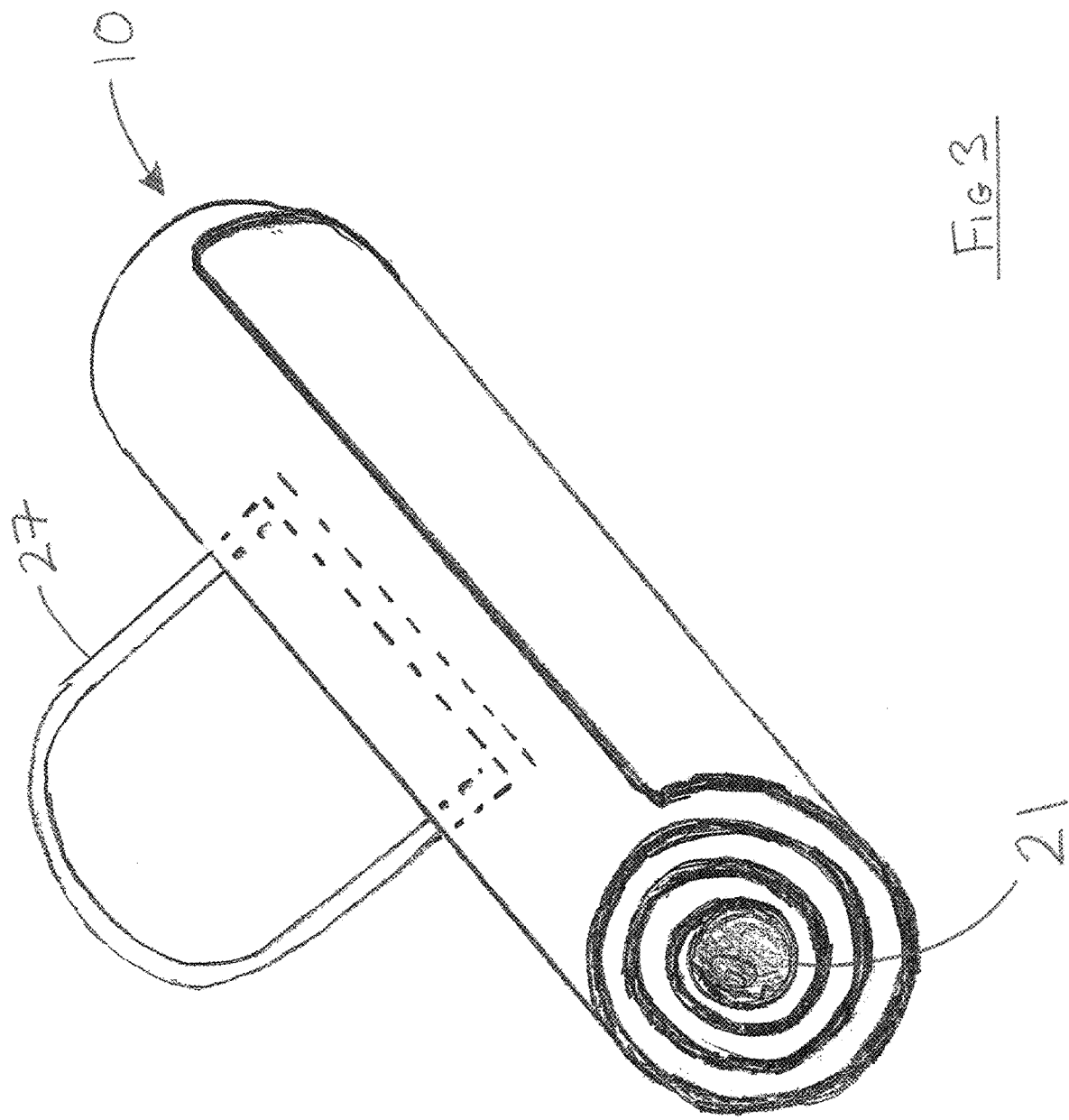
FIG. 3 is a perspective view illustrative of the portable sanitary staging assembly of FIG. 1 disposed in a closed orientation for transport or storage in accordance with the present invention.

FIG. 1 is further illustrative of one embodiment of a portable sanitary staging assembly 10 including a sanitary pad assembly 30, as noted above. In one embodiment of the present invention, a sanitary pad assembly 30 includes a sanitary main pad 32. In accordance with the illustrative embodiment of FIG. 1, the sanitary pad assembly 30 further comprises a plurality of sanitary flaps 34. The plurality of sanitary flaps 34 as illustrated in FIGS. 1, 1A and 2 are disposed in an open orientation thereby providing additional sanitary staging area for a baby or a person or animal, such as for triage or emergency field medical treatment, or for receiving medical attention outside of a typical medical environment. Each of the plurality of sanitary flaps 34 may be folded over onto the main sanitary pad 32 along the dashed lines shown in the illustrative embodiment of FIGS. 1, 1A, and 2 to facilitate disposition of a portable sanitary staging assembly 10 in accordance with the present invention into a closed orientation to facilitate transport or storage, such as is shown best in the illustrative embodiment of FIG. 3. With further reference to the illustrative embodiment of FIG. 3, in at least one embodiment, a portable sanitary staging assembly 10 in accordance with the present invention comprises a handle 27 attached there to further facilitate transport and/or storage.

It will be appreciated by those of skill in the art that a sanitary pad assembly 30 in accordance with the present invention may comprise a sanitary main pad 32 without a plurality of sanitary flaps 34 attached thereto. It will also be appreciated by those of skill in the art that a sanitary pad assembly in accordance with the present invention may include a sanitary main pad 32 with a single sanitary flap 34 attached thereto.

In at least one embodiment, such as is shown in FIGS. 1, 1A, and 2, a sanitary pad assembly 30 further comprises a pouch 36. Pouch 36 is provided for the storage and transport of ancillary items as may be used in conjunction with a portable sanitary staging assembly 10. For example, where a portable sanitary staging assembly 10 in accordance with the present invention is utilized as a baby changing station, fresh diapers, baby powder, baby oil, sanitary wipes, etc., May be stored and transported in pouch 36. Alternatively, portable sanitary staging assembly 10 in accordance with the present invention is utilized to stage an injured person or animal, or to provide medical attention to a person or animal, a pouch 36 may be used to store bandages, sterile wipes, syringes, ointments, medication, surgical tools, etc. As will be appreciated by those of skill in the art, a sanitary pad assembly 30 in accordance with the present invention may comprise a plurality of pouches 36.

A sanitary main pad 32 in accordance with the present invention may be constructed with a water resistant cover material that can be washed to clean and disinfect after use, the water resistant cover material overlying a soft or resilient foam like material. Similarly, a sanitary flap 34 in accordance with the present invention may be constructed with a water resistant cover material that, once again, can be washed to clean and disinfect after use. As shown in the illustrative embodiment of FIG. 1, sanitary pad assembly 30 and the dispenser cover 26 of the sanitary paper dispenser assembly 20 comprise a unitary construction.

With reference to FIG. 1A, in at least one embodiment of the present invention, a dispenser cover 26 of a sanitary paper dispenser assembly 20 is detachable from a sanitary pad assembly 30. As further shown in the illustrative embodiment of FIG. 1A, a dispenser cover 26 includes a pad interconnect 28. Also shown in FIG. 1A is a sanitary pad assembly 30 comprising a cooperatively structured and disposed dispenser interconnect 38. In one embodiment, a pad interconnect 28 and a dispenser interconnect 38 comprise corresponding hook and loop type fasteners which cooperatively engage to removably attach a sanitary pad assembly 30 to a sanitary paper dispenser assembly 20. Of course, it will be appreciated by those of skill in the art that any of a variety of mechanical fasteners may be utilized to removably attach a sanitary paper dispenser assembly 20 to a portion of a sanitary pad assembly 30 including, by way of example only, snaps, ties, zippers, magnets, etc.

With reference once again to the illustrative embodiment of FIG. 1, a portable sanitary staging assembly 10 in accordance with the present invention further comprises a cutter mechanism 40. More in particular, a portable sanitary staging assembly 10 comprises a cutter mechanism 40 structured to facilitate removal of soiled sanitary paper ("SP") after use. As further illustrated in FIG. 1, in at least one embodiment, a cutter mechanism 40 includes a cutter bar 42 attached to a portion of the sanitary paper dispenser assembly 20. Looking to the illustrative embodiment of FIG.

7, is seen that cutter bar 42 of cutter mechanism 40 is attached to a portion of sanitary paper dispenser assembly 20 in a manner so as to form a cutter slot 44 between the cutter bar 42 and the sanitary paper dispenser assembly 20. As further illustrated in FIG. 7, the cutter slot 44 is dimensioned to receive an amount of the sanitary paper ("SP") therethrough. A cutter bar 42 in accordance with the present invention may be constructed from any of a variety of rigid or semi rigid materials including, but not limited to plastics, metals, alloys, composite materials, etc. In at least one embodiment, a cutter bar 42 is constructed of polycarbonate such that it may be attached by sewing to a portion of a portable sanitary staging assembly 10. It will be further appreciated by those of skill in the art that a cutter bar 42 in at least one embodiment of the present invention may comprise a serrated edge to facilitate removal of the sanitary paper after use.

Figure 4:
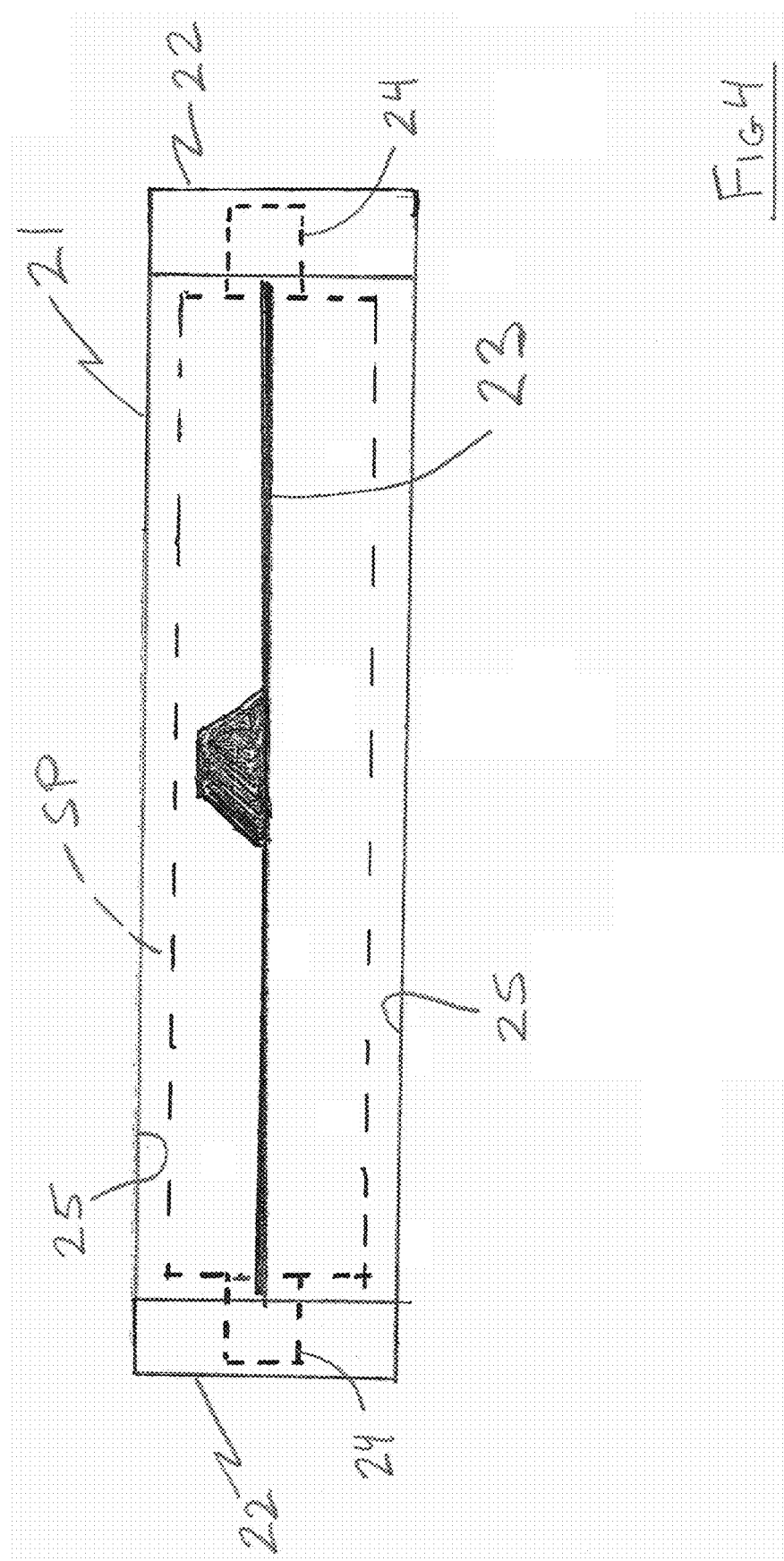
FIG. 4 is a front elevation illustrative of one embodiment of a dispenser/protector tube in accordance with the present invention.

Turning next to FIG. 4, a dispenser/protector tube 21 in accordance with one embodiment of the present invention is illustrated. As shown in the illustrative embodiment of FIG. 4, dispenser/protector tube 21 comprises end caps 22 disposed on opposite ends thereof. At least one of end caps 22 is removably attached to dispenser/protector tube 21 to permit access to the interior thereof to allow for the addition and/or replacement of sanitary paper ("SP"). A dispenser/protector tube in accordance with the present invention may be constructed of any of a variety of rigid or semi-rigid materials such as, by way of example only, plastic, paper, board, acrylic, etc.

As shown in the illustrative embodiment of FIG. 4, the sanitary paper ("SP") is provided in a continuous roll. However, it will be appreciated by those of skill in the art that sanitary paper ("SP") in accordance with the present invention may comprise a plurality of individual sheets having interlocking interfolded leaves, such as facial tissue paper, and dimensioned to extend the length of the sanitary pad assembly 20. In at least one embodiment, the sanitary paper ("SP") comprises medical grade paper, such as is used in doctor's offices and diagnostic facilities for patients to sit or lie upon.

With further reference to FIG. 4, a dispenser/protector tube 21 in accordance with the present invention includes a dispenser slot 23. As shown best in FIG. 4, the dispenser slot 23 is dimensioned to receive the full width of the sanitary paper ("SP") therethrough. FIG. 4 is also illustrative of an embodiment of a sanitary paper dispenser assembly 20 including a plurality of paper supports 24. As may be seen from FIG. 4, the plurality of paper supports 24 cooperatively engage the roll of sanitary paper ("SP") and maintain the roll of sanitary paper ("SP") in an operative orientation within dispenser/protector tube 21. More in particular, the operative orientation of the roll of sanitary paper ("SP") is at least partially defined by the roll of sanitary paper ("SP") being supported off of an interior surface 25 of the dispenser/protector tube 21, as shown best in the illustrative embodiment of FIG. 4.

An exploded perspective view of a dispenser/protector tube 21 including a dispenser slot 23 and having a plurality of end caps 22 and a corresponding plurality of paper supports 24 to maintain a roll of sanitary paper ("SP") in an operative orientation is presented in the illustrative embodiment of FIG. 5.

Turning once again to the illustrative embodiment of FIG. 2, one embodiment of a portable sanitary staging assembly 10 is presented in an open operative orientation. As may be seen from FIG. 2, a portion of sanitary paper ("SP") is disposed from dispenser/protector tube 21 under cutter bar 42 in a covering relation to sanitary main pad 32 of sanitary pad assembly 30. As such, an infant or a baby being changed may be placed on the portion of sanitary paper ("SP") covering sanitary main pad 32 while the infant's or baby's diaper is being changed. After changing the diaper, the portion of sanitary paper ("SP") on which the infant or baby was placed while being changed is pulled up and along the edge of cutter bar 42 to facilitate removal of the soiled sanitary paper which may then be readily disposed of with the soiled diaper. When the infant's or baby's diaper needs to be changed again, a user of the present portable sanitary staging assembly 10 simply pulls a clean fresh portion of sanitary paper ("SP") from the dispenser/protector tube 21 under cutter bar 42 and into a covering relation to sanitary main pad 32.

Similarly, when the present portable sanitary staging assembly 10 is utilized to stage an injured person or animal, such as for triage or emergency field medical treatment, or for a person or animal receiving medical attention outside of a typical medical environment, a user of the present portable sanitary staging assembly 10 simply pulls a clean fresh portion of sanitary paper ("SP") from the dispenser/protector tube 21 under cutter bar 42 and into a covering relation to sanitary main pad 32. As before, when the procedure is completed, the user simply removes the portion of sanitary paper ("SP") on which the person or animal was staged by pulling up and along the edge of cutter bar 42 to facilitate disposal of the soiled sanitary paper.

Turning now to the illustrative embodiment of FIGS. 6 and 7, one alternate embodiment of a portable sanitary staging assembly 10' is presented. As may be seen from FIGS. 6 and 7, the alternate embodiment of a portable sanitary staging assembly 10' includes a sanitary paper dispenser assembly 20 and a cutter mechanism 40, as before. However, as shown best in FIG. 6, the alternate embodiment of a portable sanitary staging assembly 10' does not include a sanitary pad assembly 30 as was disclosed above with reference to FIGS. 1, 1A, and 2. The alternate embodiment of a portable sanitary staging assembly 10', as shown in the illustrative embodiments of FIGS. 6 and 7, is structured to be more compact to further facilitate transport and/or storage which may be more critical in certain situations, such as, by way of example only, combat zones, natural disaster sites, terrorist attack sites, etc. More in particular, the alternate embodiment of a portable sanitary staging assembly 10' as shown in FIGS. 6 and 7, is intended to be deployed on any generally flat surface such as a table, floor, desk, sidewalk, street, etc. A sanitary paper dispenser assembly 20 in accordance with the present invention may utilize double-sided tape, hook and loop type fasteners, ties, magnets, etc., to retain the sanitary paper dispenser assembly 20 in position on the generally flat surface on which the portable sanitary staging assembly 10' is deployed.

As before, the alternate embodiment of a portable sanitary staging assembly 10' comprises a sanitary paper dispenser assembly 20 having a dispenser cover 26. Further, the dispenser cover 26 is dimensioned to receive at least a portion of a dispenser/protector tube 21 therein. An amount of sanitary paper ("SP"), for example, a roll of sanitary paper ("SP"), is received within dispenser/protector tube 21. Also as before, a cutter mechanism 40 comprising a cutter bar 42 is affixed to a portion of the sanitary paper dispenser assembly 20 such that a cutter slot 44 is formed between the cutter bar 42 and the sanitary paper dispenser assembly 20 such that a portion of the sanitary paper ("SP") may be dispensed therethrough.

With further reference to the illustrative embodiment of FIG. 6, an alternate embodiment of a portable sanitary staging assembly 10' further comprises a paper hold 46. More in particular, a paper hold 46 is used to hold a portion of the sanitary paper ("SP") in position thereunder, while a person or animal is staged on the sanitary paper ("SP"). A paper hold 46 in accordance with the present invention may include double-sided tape, hook and loop type fasteners, magnets, etc., on both ends in order to retain the paper hold down 46 in position on the generally flat surface on which the portable sanitary staging assembly 10' is deployed. A paper hold 46 in accordance with the present invention may be constructed of a variety of materials such as, paper, plastic, metal, composite materials, etc. Further, a paper hold 46 may be constructed of material to be disposable after a single use along with the soiled sanitary paper ("SP"), or in at least one further embodiment, a paper hold 46 is constructed of material which may be cleaned and sanitized for reuse.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A portable sanitary staging assembly comprising:
    a sanitary paper dispenser assembly, said sanitary paper dispenser assembly comprising a dispenser/protector tube dimensioned to receive a roll of sanitary paper therein, said dispenser/protector tube having a dispenser slot formed through a portion thereof to facilitate dispensing the sanitary paper therethrough,
    a sanitary pad assembly comprising a main sanitary pad, said sanitary pad assembly interconnected to a portion of said sanitary paper dispenser assembly, and
    a cutter mechanism to facilitate removal of soiled sanitary paper after use.

2. The portable sanitary staging assembly as recited in claim 1 wherein said sanitary paper dispenser assembly further comprises at least one paper support to maintain the roll of sanitary paper in an operative orientation.

3. The portable sanitary staging assembly as recited in claim 2 wherein said operative orientation is at least partially defined by the roll of sanitary paper supported off of an inner surface of said dispenser/protector tube.

4. The portable sanitary staging assembly as recited in claim 1 wherein said sanitary paper dispenser assembly further comprises a dispenser cover dimensioned to receive at least a portion of said dispenser/protector tube therein.

5. The portable sanitary staging assembly as recited in claim 1 wherein said sanitary pad assembly further comprises at least one sanitary flap attached to a portion of said main sanitary pad, said sanitary flap disposable between an open orientation and a closed orientation, said open orientation providing additional sanitary staging area for staging a person or an animal.

6. The portable sanitary staging assembly as recited in claim 1 wherein said pad assembly further comprises a plurality of sanitary flaps attached to different portions of said main pad, each of said sanitary flaps disposable between an open orientation and a closed orientation, said open orientation providing additional sanitary staging area for staging a person or an animal.

7. The portable sanitary staging assembly as recited in claim 1 wherein said cutter mechanism comprises a cutter bar affixed to a portion of said sanitary paper dispenser assembly.

8. The portable sanitary staging assembly as recited in claim 7 wherein said cutter mechanism further comprises a cutter slot under said cutter bar, said cutter slot dimensioned to receive a portion of the sanitary paper therethrough.

9. The portable sanitary staging assembly as recited in claim 1 further comprising a paper hold dimensioned to receive a portion of the sanitary paper thereunder to retain the portion of the sanitary paper in place while a person or animal is staged thereon.

10. The portable sanitary staging assembly as recited in claim 1 wherein said dispenser cover and said sanitary pad assembly comprise a unitary construction.

11. The portable sanitary staging assembly as recited in claim 1 further comprising a handle affixed to a portion thereof to facilitate transport.

12. The portable sanitary staging assembly as recited in claim 1 wherein said sanitary pad assembly further comprises at least one pouch for storage and transport of ancillary items.

13. A portable sanitary staging assembly comprising:
    a sanitary paper dispenser assembly, said sanitary paper dispenser assembly comprising a dispenser/protector tube having a dispenser slot formed through a portion thereof to facilitate dispensing sanitary paper therethrough,
    said sanitary paper dispenser assembly further comprising a dispenser cover dimensioned to receive at least a portion of said dispenser/protector tube therein, and
    a cutter mechanism comprising a cutter bar affixed to a portion of said sanitary paper dispenser assembly to facilitate removal of soiled sanitary paper after use.

14. The portable sanitary staging assembly as recited in claim 13 wherein said sanitary paper dispenser assembly further comprises at least one paper support to maintain the roll of sanitary paper in an operative orientation.

15. The portable sanitary staging assembly as recited in claim 14 wherein said operative orientation is at least partially defined by the roll of sanitary paper supported off of an inner surface of said dispenser/protector tube.

16. The portable sanitary staging assembly as recited in claim 13 wherein said cutter mechanism comprises a cutter bar affixed to a portion of said dispenser cover.

17. The portable sanitary staging assembly as recited in claim 16 wherein said cutter mechanism further comprises a cutter slot under said cutter bar, said cutter slot dimensioned to receive a portion of the sanitary paper therethrough.

18. The portable sanitary staging assembly as recited in claim 13 further comprising a paper hold dimensioned to receive a portion of the sanitary paper thereunder to retain the portion of the sanitary paper in place while a person or animal is staged thereon.

19. The portable sanitary staging assembly as recited in claim 13 further comprising a handle affixed to a portion thereof to facilitate transport.

20. A portable sanitary staging assembly comprising:
    a sanitary paper dispenser assembly, said sanitary paper dispenser assembly comprising a dispenser/protector tube having a dispenser slot formed through a portion thereof to facilitate dispensing sanitary paper therethrough,
    said sanitary paper dispenser assembly further comprising a dispenser cover dimensioned to receive at least a portion of said dispenser/protector tube therein, a sanitary pad assembly comprising a main pad, said pad assembly interconnected to a portion of said sanitary paper dispenser assembly, said sanitary pad assembly further comprising at least one sanitary flap attached to a portion of said main sanitary pad, said sanitary flap disposable between an open orientation and a closed orientation, said open orientation providing additional sanitary staging area for staging a person or an animal, a cutter mechanism comprising a cutter bar to facilitate removal of soiled sanitary paper after use, said cutter mechanism further comprises a cutter slot under said cutter bar, said cutter slot dimensioned to receive a portion of the sanitary paper therethrough, and a paper hold dimensioned to receive a portion of the sanitary paper thereunder to retain the portion of the sanitary paper in place while a person or animal is staged thereon.

* * * * *